United States Patent
Brown

(10) Patent No.: US 8,216,450 B2
(45) Date of Patent: Jul. 10, 2012

(54) REMOVAL OF BROMINE INDEX CONTAMINANTS FROM AROMATIC STREAMS

(75) Inventor: Stephen H. Brown, Bernardsville, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 292 days.

(21) Appl. No.: 12/758,388

(22) Filed: Apr. 12, 2010

(65) Prior Publication Data

US 2010/0274064 A1 Oct. 28, 2010

Related U.S. Application Data

(60) Provisional application No. 61/171,549, filed on Apr. 22, 2009.

(51) Int. Cl.
*C07C 5/08* (2006.01)

(52) U.S. Cl. ........ 208/299; 208/295; 208/307; 208/263; 585/258; 585/259; 585/260; 585/261; 585/264

(58) Field of Classification Search .................. None
See application file for complete search history.

(56) References Cited

U.S. PATENT DOCUMENTS

| | | | |
|---|---|---|---|
| 6,368,496 B1 | 4/2002 | Brown et al. | |
| 6,500,996 B1 | 12/2002 | Brown et al. | |
| 6,781,023 B2 | 8/2004 | Brown et al. | |
| 7,744,750 B2* | 6/2010 | Brown et al. | 208/299 |
| 7,815,793 B2* | 10/2010 | Brown et al. | 208/299 |
| 2003/0032850 A1* | 2/2003 | Brown et al. | 585/804 |
| 2006/0270886 A1 | 11/2006 | Brown et al. | |
| 2007/0112239 A1 | 5/2007 | Brown et al. | |
| 2007/0112240 A1 | 5/2007 | Brown et al. | |
| 2007/0129235 A1 | 6/2007 | Brown et al. | |
| 2008/0128329 A1 | 6/2008 | Brown et al. | |

FOREIGN PATENT DOCUMENTS

| | | |
|---|---|---|
| WO | 94/00409 | 1/1994 |
| WO | 01/23502 | 4/2001 |
| WO | 01/30942 | 5/2001 |
| WO | 2008/070297 | 6/2008 |

* cited by examiner

*Primary Examiner* — Tam M Nguyen
(74) *Attorney, Agent, or Firm* — Andrew B. Griffis

(57) ABSTRACT

According to the invention, trace olefins and dienes are removed from aromatic plant feedstocks by contacting the catalyst using conditions outside the ordinary range used for this application today.

9 Claims, 2 Drawing Sheets

REMOVAL OF BROMINE INDEX CONTAMINANTS FROM AROMATIC STREAMS

CROSS REFERENCE TO RELATED APPLICATIONS

This application claims the benefit of Provisional Application No. 61/171,549 filed Apr. 22, 2009, the disclosure of which is incorporated by reference in its entirety.

FIELD OF THE INVENTION

The invention relates to the treatment of aromatic streams to improve downstream processing.

BACKGROUND OF THE INVENTION

In petroleum processing, aromatic streams are derived from processes such as naphtha reforming and thermal cracking (pyrolysis). These aromatic streams also contain undesirable hydrocarbon contaminants including mono-olefins, dienes, styrenes and heavy aromatic compounds such as anthracenes.

The aromatic streams are used as feedstocks in various subsequent petrochemical processes. In certain of these processes, such as para-xylene production, e.g., from an aromatic stream containing benzene, toluene and xylene (BTX) or toluene disproportionation, hydrocarbon contaminants cause undesirable side reactions. Therefore the hydrocarbon contaminants must be removed before subsequent processing of the aromatic streams.

Moreover, the shift from high-pressure semiregenerative reformers to low-pressure moving bed reformers results in a substantial increase in contaminants in the reformate derived streams. This in turn results in a greater need for more efficient and less expensive methods for removal of hydrocarbon contaminants from the aromatic streams.

Undesirable hydrocarbon contaminants containing olefinic bonds are quantified by the Bromine Index (BI). Undesirable olefins, including both dienes and mono-olefins, have typically been concurrently removed from aromatic streams such as BTX by contacting the aromatic stream with acid-treated clay. Other materials, e.g., zeolites, have also been used for this purpose. Clay is an amorphous naturally-occurring material, while zeolites used for this purpose generally are synthesized and are therefore more expensive. Both clay and zeolites have very limited lifetimes in aromatics treatment services. The length of service correlates with the level of bromine reactive impurities ("BI-reactive" impurities or contaminants) in the feedstream. BI-reactive contaminants rapidly age both clay and zeolites. Indeed, although clay is the less expensive of the two alternatives, large aromatic plants can spend more than a million dollars a year on clay. Furthermore, since zeolites are considerably more expensive than clay, their use in removing hydrocarbon contaminants can only be justified by dramatically improved stability in aromatics treatment so that their cycle length is practical.

U.S. Pat. Nos. 6,368,496 and 6,781,023 teach bromine reactive hydrocarbon contaminants are removed from aromatic streams by first providing an aromatic feedstream having a negligible diene level. The feedstream is contacted with an acid active zeolite catalyst composition under conditions sufficient to remove mono-olefins. The aromatic stream may be pretreated to remove dienes by contacting the stream with clay, hydrogenation or hydrotreating catalyst under conditions sufficient to substantially remove dienes but not mono-lefins.

Other relevant references include, U.S. Pat. Nos. 6,500, 996; 6,781,023 and U.S. Patent Application Publications 20060270886; 20070112240; 20070112239; 20070129235; and 20080128329.

Current clay treater reactor designs typically have a feed pre-heater capable of heating the feed to a maximum of 205° C., and operate at a maximum of 2 WHSV. Also, conventional clay treater designs do not have the capability of recycling product. The current features limit the optimization potential when using zeolites in place of clay.

The present inventor has surprisingly discovered a method of reducing the cost and reducing the environmental impact of the current process used to remove olefins from aromatics plant feedstocks, which in embodiments is achieved by operating zeolite treatment reactors similar to continuous stirred tank reactors (CSTR).

SUMMARY OF THE INVENTION

The invention is directed to the removal of trace olefins and dienes from aromatic feedstocks using conditions outside the ordinary range currently used.

In embodiments, at the start of the cycle the feed is heated and contacts the zeolite catalyst above temperatures currently used, such as about 210° C., and the temperature is gradually increased to between about 240 and 300° C. at the end of the cycle. These temperatures can be achieved by revamping the existing equipment, or by replacing the existing reactor system with a new reactor system, or by building a new reactor system.

In embodiments the feed is passed over the catalyst at between about 7 and about 20 WHSV at optimal conditions.

In still other embodiments removal of trace olefins and dienes is carried out in the presence of recycled reactor product. Recirculation of product without addition of fresh feed provides an unexpected method of rejuvenating the catalyst system.

In yet still other embodiments, recirculation of product while processing fresh feed unexpectedly increases cycle length.

It is an object of the invention to improve the removal of impurities from aromatic streams in a method that also increases the yield of product and decreases the cost of such removal.

These and other objects, features, and advantages will become apparent as reference is made to the following detailed description, preferred embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
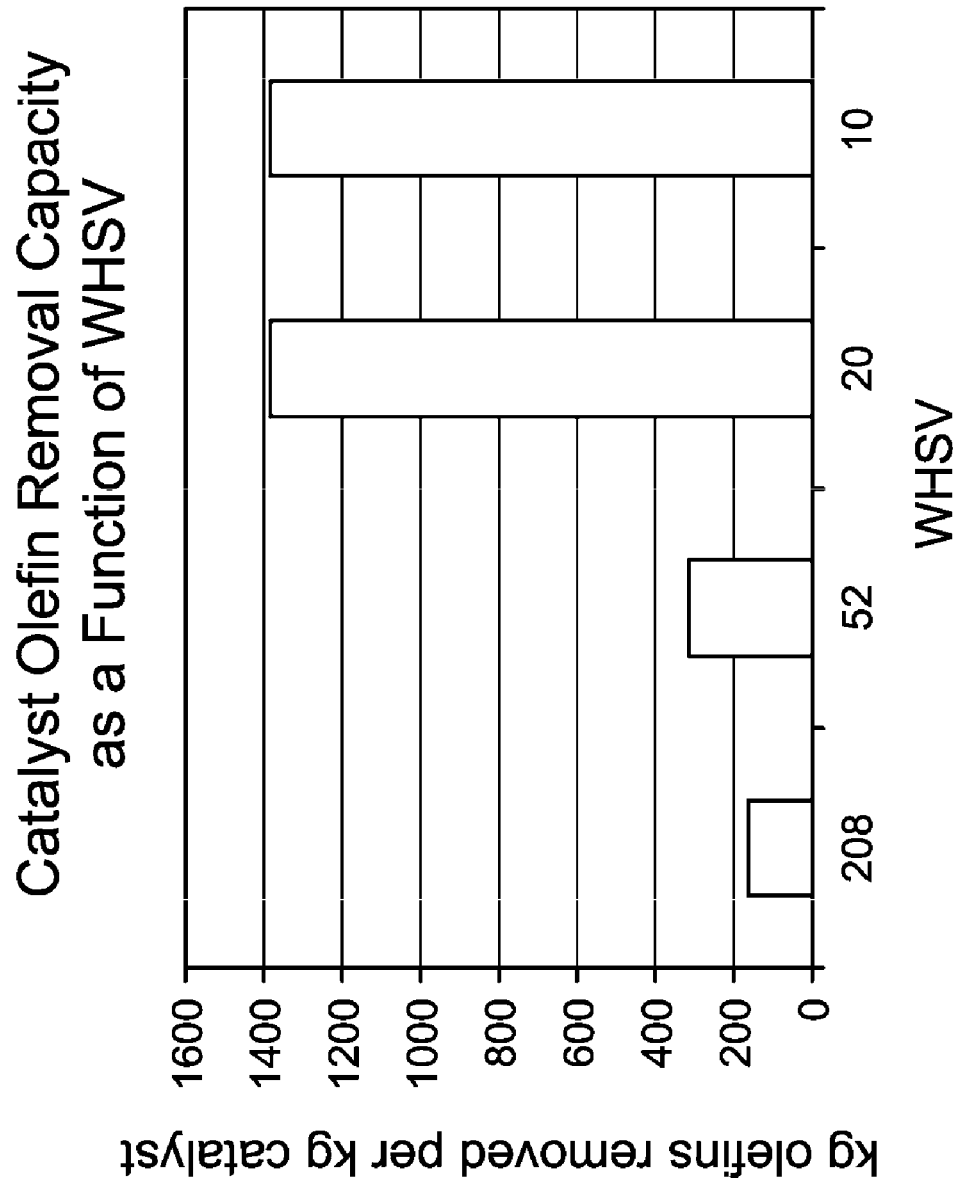
FIG. 1 is a graph showing olefin impurity removal capacity as a function of WHSV for an embodiment of the invention.

The feedstreams of the invention may be pretreated in order to have negligible levels of dienes.

An aromatic hydrocarbon stream to be treated to remove mono-olefins according to the invention is essentially diene-free, i.e., has a negligible level of dienes. If the aromatic stream contains dienes above these levels, the stream can be pre-treated according to the invention to remove the dienes. Dienes are more selective for catalyst deactivating coke formation than mono-olefins. Therefore, these highly reactive diene species are substantially removed over a first catalyst. One of ordinary skill in the art in possession of the present disclosure can determine the appropriate level of dienes present without more than routine experimentation. In embodiments, the amount of dienes will be less than 1000 ppm and a feed such as reformate having less than 1000 ppm dienes is preferred. Another preferred feed is one having 10,000 ppm total olefins or less, including styrenes and dienes, wherein the dienes are present in the amount of no more than 10 wt % of the total BI. Feeds having less than 1000 ppm or less than 500 ppm or less than 300 ppm or less than 100 ppm dienes are also preferred. There is no particular minimum amount of dienes that needs to be specified, however in embodiments it will be specified that dienes are present, or that dienes are present in the amount of at least 1 ppm, or 10 ppm, or 100 ppm. In a process according to the invention, the catalyst has excellent stability even for commercial feeds having the highest diene levels to be expected.

The pre-treating step is conducted at temperatures preferably of about 50 or 100° F. (10° C. and 38° C., respectively). to about 500° F. (260° C.) or 600° F. (316° C.), more preferably about 150° F. (65° C.) to about 450° F. (232° C.). A weight hourly space velocity (WHSV) is preferably from about 0.1 to about 10 and the pressure is preferably about 50 psig to about 500 psig. The pre-treating is carried out in the absence of added hydrogen. Preferred catalysts for the pre-treatment step include acid treated clay such as bentonite or traditional base metal-containing hydrogenation or hydrotreating catalysts such as $NiMo/Al_2O_3$, $CoMo/Al_2O_3$, $Ni/Al_2O_3$ and $Ni/SiO_2$.

In embodiments, the thusly pre-treated aromatic feed is then treated over a second catalyst to substantially remove the mono-olefins, as described herein below.

According to the invention, trace olefins and dienes are removed from aromatic plant feedstocks by contacting the catalyst using conditions outside the ordinary range used for this application today. In an embodiment, the feed is heated above the capability of current commercial clay treaters, such as to 210° C., or 215° C., or 220° C., at the start of the contact cycle. Typical commercial clay treaters have a 205° C. maximum feed temperature. Heater capable of temperatures according to the present invention are available.

The reaction continues to an end of cycle temperature, which may conveniently be between about 240 and about 300° C., such as 250° C., 260° C., 270° C., or 280° C. Surprisingly, the catalyst has similar selectivity and stability in this higher temperature window. The catalyst is much more active in the higher temperature window. In embodiments, the catalyst may also be contacted using high WHSV of greater than 5 to less than 30, such as between 10 and 20 WHSV at such temperatures. This is much higher than the 0.5 to 2 WHSV typically used in today's reactors. Surprisingly, the catalyst is stable for many months despite the much smaller volume of catalyst charged.

Operation at high WHSV requires operation at high temperature. The incentives to run in a CSTR mode will vary depending upon the feedstock and catalyst. Likewise the incentives to practice on-line rejuvenations in-between air regenerations will vary with feedstock and catalyst. Those skilled in the art will use different combinations in order to optimize operations.

Zeolite catalysts contain Bronsted acid sites distributed across a surface area typically between 100 and 500 m2/g. During the course of aromatics pretreatment, carbonaceous deposits accumulate on the catalyst and block access to acid sites. Therefore the number of accessible acid sites declines with time on stream. The minimum number of acid sites required to accomplish the required conversion of olefin impurities depends upon the reactor temperature and flowrate. As the reactor temperature rises, each acid site converts more olefins per unit of time (each acid site has a higher turnover frequency), and fewer sites are needed. As the feedstock flowrate increases, more olefins must be converted by the fixed number of acid sites. Since higher reactor temperature increases the capacity of each acid site to convert olefins, higher reactor temperature enables unit operation at higher WHSV. Higher reactor temperature is also used to compensate for coke deposition with time. As coke accumulation steadily blocks sites with time, raising the reactor temperature increases the amount of olefins converted by the remaining accessible acid sites. Pushing reactor temperatures above 240° C. allows operation of catalyst having coke loadings as high as 50 wt % of the removed catalyst. Removal of trace olefins and dienes from the feedstock is preferably carried out in the presence of recycled reactor product. This novel means of operation provides two unexpected benefits. Recirculation of product without addition of fresh feed provides an unexpected means of rejuvenating the catalyst system. Recirculation of product while processing fresh feed unexpectedly increases cycle length. Without wishing to be bound by theory, the benefit may be achieved by more evenly distributing the reaction workload from the top to the bottom of the bed.

Coke is a byproduct of the reaction that removes contaminant olefins, dienes, and styrenes from aromatics plant feedstocks. Coke selectivity is difficult to predict. The inventors surprisingly discovered that the coke selectivity for BI reduction of aromatics plant feedstocks is independent of the concentration of reaction products and dependent upon the concentration of olefins and dienes in the feed. Diluting the incoming high BI feedstock with low BI reactor product, reduces the BI of the reactor feedstock and thereby reduces coke selectivity. For example, 1 part of a C8+ heavy reformate feedstock with a BI of 1000 diluted with 4 parts of reactor product with a BI of 100 results in a reactor feedstock with a BI of 280. Some heavy reformate aromatics feedstocks can have a BI of <300. For these feedstocks, the olefins and dienes are already diluted to <300 BI in reformate aromatics. The difference in BI between the feedstock and the product specification is <300. Coke selectivity is inherently low, and further dilution does not substantially reduce coke selectivity. In these cases there is little incentive to recycle reactor feedstock. On the other hand, some heavy reformate aromatics feedstocks can have a BI of >2000 ppm. The difference in BI between the feedstock and the product specification is >1500. Recycling the product can lead to a substantial reduction in coke selectivity.

The inventors surprisingly discovered that feed molecules convert to coke via reactive intermediate molecules that will desorb from the catalyst bed if they don't react with other feedstock molecules. Shutting off fresh feedstock and operating the reactor with 100% product recycle provides time to desorb these molecules. In other words, operating with 100% product recycle can wash coke precursors off the catalyst bed, thereby extending catalyst life.

The process will be described with particular emphasis on feeds, pretreatment, catalysts, process conditions, and regeneration. One of ordinary skill in the art will recognize that there are numerous variations possible within the scope of the appended claims.

Feeds

Aromatic streams can be obtained from reforming and cracking processes. The streams include, e.g., mononuclear aromatic hydrocarbons and undesirable olefins including styrenes, and the streams have an initial Bromine Index (BI) from about 100 to about 3000. The Bromine Index is an indicator of the presence of olefinic bonds. Bromine Index is determined according to ASTM D 2710-92 and is a measure of milligrams of bromine consumed by 100 grams of sample under given conditions.

The aromatics include, for example, benzene, toluene, xylene, ethyl benzene, cumene and other aromatics derived, e.g., from reformate. Reformate is separated by distillation into light reformate which is mostly benzene and toluene, and heavy reformate which includes toluene, ortho-, meta- and para-xylenes and other heavier aromatics including C9+. Some aromatic streams such as heavy reformate derived from semi-regen processes contain negligible levels of dienes as they emerge from the processing. By negligible is meant that the level is below 50 ppm, essentially diene-free or too low to be quantified. Other aromatic streams such as light reformate derived from semi-regen reformers and light and heavy reformate from CCR's (continuous catalyst regeneration) processes include detectable levels of dienes, e.g., over 50 ppm, as they emerge from the processes.

The aromatic streams to be treated according to the invention contain bromine-reactive hydrocarbon compounds in levels which interfere in subsequent aromatics processing. An objectionable level of olefinic contaminants is from about 0.05 to about 1.5 weight percent or a BI from about 100 to about 3000.

According to embodiments of the invention, use of a regenerated catalyst improves the removal of olefinic contaminants in the aromatic streams so that said contaminants do not interfere in subsequent aromatics processing.

Pre-Treatment

An aromatic hydrocarbon stream to be treated to remove mono-olefins according to the invention is essentially diene-free, i.e., has a negligible level of dienes. If the aromatic stream contains dienes above these levels, the stream can be pre-treated according to the invention to remove the dienes. Dienes are more selective for catalyst deactivating coke formation than mono-olefins. Therefore, these highly reactive diene species are substantially removed over a first catalyst.

The pre-treating step is conducted at temperatures preferably of about 50 or 100° F. (10° C. and 38° C., respectively). to about 500° F. (260° C.) or 600° F. (316° C.), more preferably about 150° F. (65° C.) to about 450° F. (232° C.). Temperature ranges from any of the aforementioned minimums to any of the aforementioned maximums are also contemplated as embodiments. In preferred embodiments using the aforementioned temperature ranges, a weight hourly space velocity (WHSV) is preferably from about 0.1 to about 10 and the pressure is preferably about 50 psig to about 500 psig. The pre-treating is carried out in the absence of added hydrogen. Preferred catalysts for the pretreatment step include acid treated clay such as bentonite or traditional base metal-containing hydrogenation or hydrotreating catalysts such as $NiMo/Al_2O_3$, $CoMo/Al_2O_3$, $Ni/Al_2O_3$ and $Ni/SiO_2$.

The pre-treated aromatic feed is then treated over a second catalyst to substantially remove the mono-olefins.

Catalysts

The catalysts for selectively removing mono-olefin compounds include, e.g., large pore zeolites, particularly MCM-22 type materials, mesoporous materials including those termed M41 S, SAPO's, pillared and/or layered materials.

Zeolites are divided into three major groups according to their pore/channel systems. These systems include 8-membered oxygen ring systems, 10-membered oxygen ring systems, 12-membered oxygen ring systems, and the dual pore systems including 10 and 12-membered oxygen ring openings. In general, they are referred to as small, medium or large pore size zeolites proceeding from 8 to 12 membered systems. These systems are more completely described in Atlas of Zeolite Structure Types, International Zeolite Assoc., Polycrystal Book Service, Plattsburg, 1978.

The chemical composition of zeolites can vary widely and they typically consist of $SiO_2$ in which some of the silicon atoms may be replaced by tetravalent ions such as Ti or Ge, or by trivalent ions such as Al, B, Ga, Fe, or by bivalent ions such as Be, or by other members of Group III of the Periodic table of the Elements or by a combination of the aforementioned ions. When there is substitution by bivalent or trivalent ions, cations such as Na+, $Ca^{++}$, $NH_4^+$ or H+ are present in the as-synthesized zeolite, also organic ions such as tetramethylamine ($TMA^+$), tetraethylamine ($TEA^+$) and others. The organics are typically removed by calcination prior to use of the zeolite. Ion exchange of residual cations with, for example, $NH_4^+$, is generally followed by calcination to produce the acidic zeolite.

Preferred catalysts include natural or synthetic crystalline molecular sieves, with ring structures of ten to twelve members or greater. Crystalline molecular sieves useful as catalysts include as non-limiting examples, large pore zeolites ZSM-4 (omega) (U.S. Pat. No. 3,923,639), mordenite, ZSM-18 (U.S. Pat. No. 3,950,496), ZSM-20 (U.S. Pat. No. 3,972,983), zeolite Beta (U.S. Pat. No. 3,308,069 and Re 28,341), Faujasite X (U.S. Pat. No. 2,882,244), Faujasite Y (U.S. Pat. No. 3,130,007), USY (U.S. Pat. Nos. 3,293,192 and 3,449,070), REY and other 15 forms of X and Y, MCM-22 (U.S. Pat. No. 4,954,325), MCM-36 (U.S. Pat. No. 5,229,341), MCM-49 (U.S. Pat. No. 5,236,575), MCM-56 (U.S. Pat. No. 5,362,697) and mesoporous materials such as M41S (U.S. Pat. No. 5,102,643) and MCM-41 (U.S. Pat. No. 5,098,684). More preferred molecular sieves include 12 membered oxygen-ring structures ZSM-12, mordenite, Zeolite Beta, USY, and the mixed 10-12 membered oxygen ring structures from the MCM-22 family, layered materials and mesoporous materials. Most preferred are the MCM-22 family of molecular sieves. This family, i.e., MCM-22 type materials, includes, e.g., MCM-22, MCM-36, MCM-49 and MCM-56. The MCM-22 type materials may be considered to contain a similar common layered structure unit. The structure unit is described, e.g., in U.S. Pat. Nos. 5,371,310, 5,453,554, 5,493,065 and 5,557,024.

One measure of acid activity may be termed the Alpha Value. The Alpha Value is an approximate indication of the catalyst acid activity and it gives the relative rate constant (rate of normal hexane conversion per volume of catalyst per unit time). It is based on the activity of the highly active silica-alumina cracking catalyst taken as an Alpha of 1 (Rate Constant=0.16 sect$^{-1}$). The alpha test is described in U.S. Pat. No. 3,354,078, in the Journal of Catalysis, Vol. 4, p. 527 (1965); Vol. 6, p. 278, and Vol. 61, p. 395 (1980), each incorporated by reference as to that description. The experimental conditions of the test used herein include a constant temperature of 538° C. and a variable flow rate as described in the Journal of Catalysis, Vol. 61, p. 395 (1980). The catalysts of the invention preferably have an alpha value from about 100 to about 1000.

The crystalline molecular sieve may be used in bound form, i.e., composited with a matrix material, including synthetic and naturally occurring substances, e.g., clay, silica, alumina, zirconia, titania, silica-alumina and other metal oxides. Naturally-occurring clays include those of the montmorillonite and kaolin families. The matrix itself may possess catalytic properties, often of an acid nature. Other porous matrix materials include silica-magnesia, silica-zirconia, silica-thoria, silica-beryllia, silica-titania, as well as ternary compositions such as silica-alumina-thoria, silica-alumina-zirconia, silica-alumina-magnesia, and silica-alumina-zirconia. A mixture of these components can also be used. The relative proportions of crystalline molecular sieve material and matrix may vary widely from 1 to 90 weight percent, usually about 20 to about 80 weight percent. The catalyst can also be used in the absence of matrix or binder, i.e., in unbound form. The catalyst can be used in the form of an extrudate, lobed form (e.g. trilobe), spheres, microspheres, or powder.

Process Conditions

Operation at high WHSV and temperature is preferred. In addition, use of a CSTR design having total liquid product recycle is preferred. High temperature requires modifications to the feed preheat equipment, and/or operating pressure. It also requires installation of equipment to enable product recycle.

In general, the method for the removal of mono-olefins is carried out under conditions including a moderately elevated temperature preferably ranging from about 200 or 250° F. (93° C. or 121° C.) to about 500° F. (260° C.), more preferably from about 250° F. (121° C.) to about 450° F. (232° C.), with ranges from any of the aforementioned minimums to the aforementioned maximums also being contemplated embodiments; a space velocity preferably ranging from about 0.1 WHSV to about 100 WHSV, more preferably from about 1 WHSV to about 30 WHSV; and a pressure ranging from about 50 psig to about 1000 psig, more preferably about 100 psig to about 500 psig.

The following non-limiting examples illustrate the invention.

COMPARATIVE EXAMPLE 1

A xylenes plant heavy reformate feedstock is treated over F-24 clay (F-24, Engelhard, Menlo Park, N.J.). A combination of fresh and recycled xylenes plant feedstock was flowed at 0.1 LHSV and 180° C. across the clay in order to remove water. The feedstock was produced by distilling the liquid product obtained from a refinery CCR to obtain a C8+ heavy reformate. The feedstock had a BI ranging from 750 to 1500 and contained <10 ppm benzene, <5000 ppm toluene, and >50 wt % C8 aromatics. Water was stripped from the product. After 3 days on stream the water in the reactor effluent dropped below 1000 ppm. The reactor conditions were then changed to 250° C. and 20 LHSV. The BI of the xylenes produced from the reactor effluent is monitored with time on stream. After 4 days the BI of the xylenes reaches the end of cycle specification of 20. The clay removed 2.5 lbs olefins/lb clay. The example shows that the conventional clay treating process is inoperable at the conditions of the invention.

EXAMPLE 2

The same xylenes plant heavy reformate feedstock with a BI of 1000 (1.5 lbs olefins per bbl) used in comparative example 1 is treated over selfbound MCM-22 catalyst at starting conditions of 10, 20, 52, and 208 LHSV and 210° C. The BI of the xylenes produced from the reactor effluent is monitored with time on stream. When the BI of the xylenes exceeded 10 temperature was raised by 10° C. increments until the reactor temperature reached 250° C. The run continued at 250° C. until the xylenes BI reached the 20 ppm specification. The amount of olefins removed per cycle as a function of LHSV is plotted in FIG. 1. The experiments prove that selfbound MCM-22 surprisingly can operate in a WHSV and temperature window outside of the operating conditions traditionally used to remove olefins from heavy reformates. The experiments surprisingly prove that selfbound MCM-22 can operate up to 20 WHSV without showing any loss in olefin removal capacity.

EXAMPLE 3

The reaction of benzene with ethylene is used to model the reaction of C6+ iso-olefins that occur in aromatics plant treatment units. Liquid feedstocks were prepared from benzene, 2-methyl-pentane, 2,3 dimethylbutane, and methylcyclopentane. The feedstock compositions are provided in Table 1. These feedstocks were blended with ethylene at mole ratios of ethylene to benzene of 0.5:1 and 1:1. The blended feedstock was processed at 2-10 WHSV, 250 psig, >98% ethylene conversion, and 350-400° F. (149-204° C.). The catalyst was an MCM-22 family molecular sieve.

TABLE 1

Feed Compositions

| | Model Isoparaffin | |
| --- | --- | --- |
| | 2,3-Dimethylpentane | 3-Methylpentane |
| Midas Number | 95-13716, -17754 | 95-29749 |
| Nominal Composition, wt % | | |
| 3-Methylpentane | — | 49.5 |
| Methylcyclopentane | 1.0 | 1.0 |
| Benzene | 49.5 | 49.5 |
| 2,3-Dimethylpentane | 49.5 | — |
| Composition (GC11), wt % | | |
| 2-Methylpentane | — | 0.047 |
| 3-Methylpentane | — | 43.791 |
| N-Hexane | 0.008 | 0.055 |
| Methylcyclopentane | 0.923 | 0.939 |
| 2,2-Dimethylpentane | 0.079 | — |
| Benzene | 51.718 | 55.163 |
| 3,3-Dimethylpentane | 0.020 | — |
| Cyclohexane | 0.012 | — |
| 2,3-Dimethylpentane | 47.021 | — |
| 3-Methylhexane | 0.183 | — |
| Toluene | — | 0.006 |
| Other C$_7$ | 0.037 | — |
| Total | 100.001 | 100.001 |
| EB Impurities*, ppmw | | |
| Range = 0 vs Range = 4 | 21 | 20 |
| Internal Standard | 34.30 | — |

Figure 2:
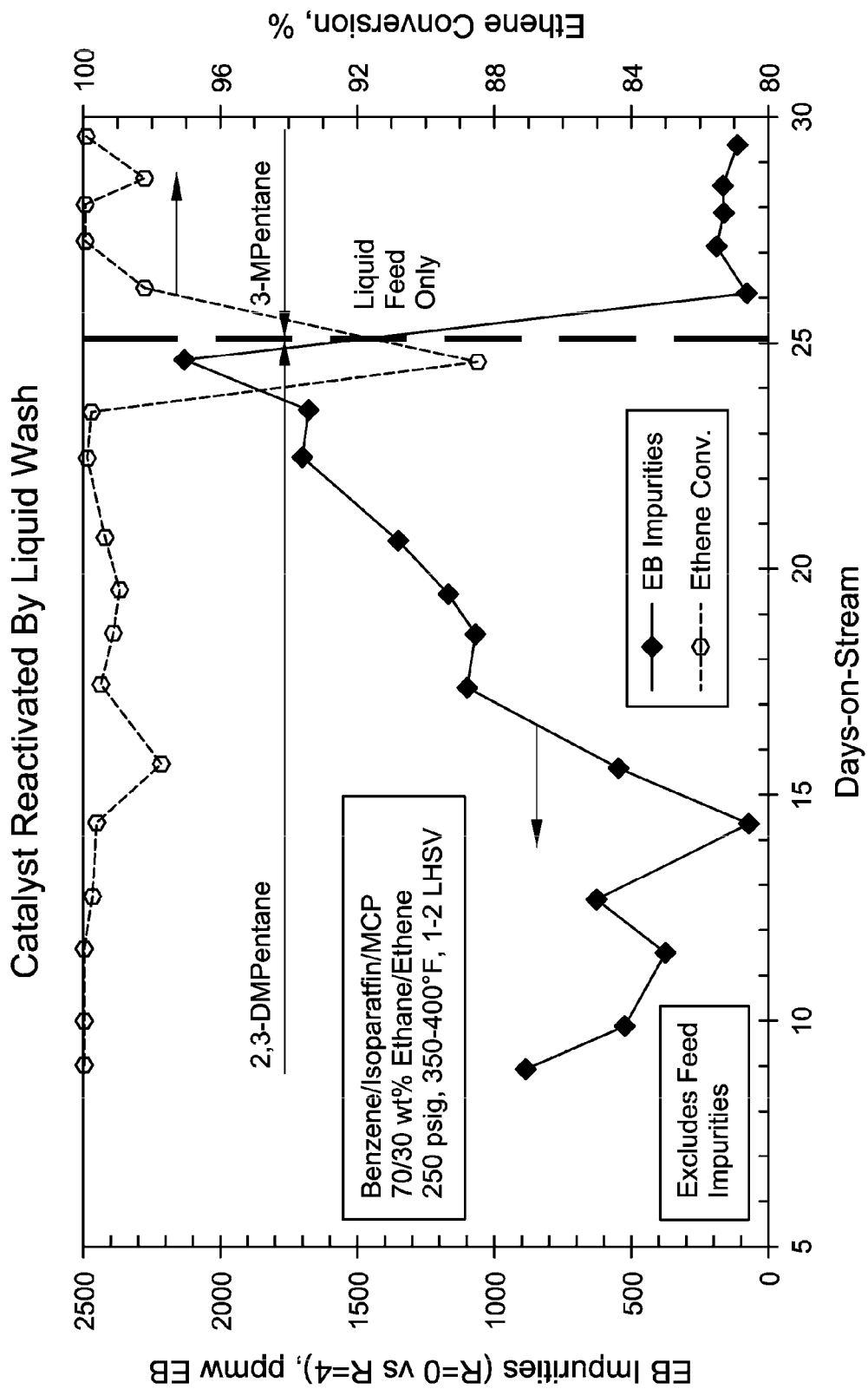
FIG. 2 is a graph of ethyl benzene impurities as a function of days on stream (DOS) for an embodiment of the invention.

*All non-EB compounds eluting between toluene and cumene on a boiling point column Catalyst performance with days on stream (DOS) is plotted in FIG. 2. The catalyst aged steadily during the first 24 DOS as evidenced by rising levels of impurities and a steep fall off in ethylene conversion after 22 days on stream. At this time, ethylene was removed from the feedstock while remaining at constant temperature, pressure, and benzene flowrate for 12 hrs. Surprisingly, this procedure restored the catalyst to fresh activity and selectivity.

The rejuvenation procedure is accomplished in an aromatics feed pre-treater by recycling the feedstock. For example, a heavy reformate feedstock comprised mostly of xylenes and C9 aromatics is passed through a reactor with MCM-22 catalyst at 0.1 to 5 LHSV, 210 to 280° C., and 250 to 500 psig. Olefins are removed. The olefin-free product is recycled to the reactor (e.g., by a recycle pump). The fresh feed is stopped. As a result, the feedstock to the reactor is free of olefins. Those skilled in the art will recognize that the olefin-free xylenes and C9 aromatics have similar properties to the benzene in Example 3 and will also effectively rejuvenate the catalyst.

COMPARATIVE EXAMPLE 4

A combination of fresh and recycled xylenes plant feedstock is flowed at 0.1 LHSV and 180° C. across a catalyst system comprising 60 vol % MCM-22 catalyst on top of 40 vol % clay catalyst in order to remove water from the catalyst/clay system. The feedstock is produced by distilling the liquid product obtained from a refinery CCR to obtain a C8+ heavy reformate. The feedstock has a BI ranging from 750 to 1500 and contains <10 ppm benzene, <5000 ppm toluene, and >50 wt % C8 aromatics. Water is stripped from the product. After 3 days on stream the water in the reactor effluent drops below 1000 ppm. The main feedstock flow is then switched to the newly dried reactor. The fresh, dry commercial catalyst is now operating at 5 LHSV and 210° C. The reactor is equipped with a system to recycle product. The recycle system is not used. The reactor effluent is <200 BI. Over the course of 6 months, the reactor temperature is raised to the unit maximum temperature of 260° C. to keep the effluent below 200 BI. At this point, the catalyst is no longer sufficiently active and the reactor is shut down to change the catalyst.

EXAMPLE 5

A combination of fresh and recycled xylenes plant feedstock is flowed at 0.1 LHSV and 180° C. across a catalyst system comprising 60 vol % MCM-22 catalyst on top of 40 vol % clay catalyst in order to remove water from the catalyst/clay system. The feedstock is produced by distilling the liquid product obtained from a refinery CCR to obtain a C8+ heavy reformate. The feedstock has a BI ranging from 750 to 1500 and contains <10 ppm benzene, <5000 ppm toluene, and >50 wt % C8 aromatics. Water is stripped from the product. After 3 days on stream the water in the reactor effluent drops below 1000 ppm. The main feedstock flow is then switched to the newly dried reactor. The fresh, dry commercial catalyst is now operating at 5 LHSV and 210° C. The reactor is equipped with a system to recycle product. The recycle system is turned on at a rate of 15 LHSV. 3 volumes of <200 BI reactor product are mixed with one volume of 1000 BI fresh feed. The combined fresh plus recycle feed enters the reactor with a BI near 400 and passes athrough the reactor at 20 LHSV. Over the course of 10 months, the reactor temperature is raised to the unit maximum temperature of 260° C. to keep the effluent below 200 BI. At this point, the recycle ratio is steadily reduced to keep the effluent below 200 BI. After 12 months the reactor is running at 5 LHSV fresh feed, 260° C., and the recycle system is off. At this point, the catalyst is no longer sufficiently active and the reactor is shut down to change the catalyst.

This example demonstrates the usefulness of continuous operation of the unit with recycle. The catalyst lasts 12 months with a 3:1 product to fresh feed recycle ratio vs. 6 months without recycle.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

The invention has been described above with reference to numerous embodiments and specific examples. Many variations will suggest themselves to those skilled in this art in light of the above detailed description. Never the less, the following sets forth the most preferred embodiments: a method for purifying an aromatic feedstream including operating at higher temperatures and WHSV conditions than is ordinarily commercially practices and providing a relatively pure aromatics feedstream having negligible levels of olefins, such as one pre-treated with clay, to a catalyst system and in preferable embodiments recycling product whereby catalyst life may be prolonged and also in embodiments rejuvenating spent catalyst by running the process on pure product. The preferred process may also be described more particularly as follows: in a method for removing bromine-reactive contaminants from an aromatic hydrocarbon feedstream having less than 1000 ppm dienes and less than 10,000 ppm total olefins (although it is understood that the invention is not so narrowly restricted to such feedstream), comprising contacting a zeolite catalyst (very preferably one from the MCM-22 family of molecular sieves) with said feedstream for a period of time defined as a contact cycle time (which may be hours or days or months, such as 10 or 20 or 30 or 100 days or even longer, such as a year or more), wherein the improvement includes conditions, said conditions comprising heating said feedstream to a temperature in the range of (or "providing a feedstream having a temperature of") at least 210° C., preferably at least 215° C., or at least 220° C., or at least 225° C., at the start of the contact cycle time to a temperature in the range of about 240 to about 300° C., preferably between about 250° C. to about 300° C., or about 260° C. to about 300° C., or about 270° C. to about 300° C., or about 280° C. to about 300° C. at the end of said contact cycle time, and a WHSV of greater than 5 and less than 30, preferably between about 10 and 20, whereby said contaminants are removed at a rate of at least 1000 kg (or at least 1200 kg or at least 1400 kg) of olefins per kg of catalyst to produce a substantially olefin-free aromatics stream (such as a BI<300 in the case of a feedstream having a BI of at least 1000, or even a BI of 50 or less in the case of certain feedstocks having a BI of between 100 and 3000) during said cycle time, and yet still more preferred embodiments, such as wherein said feed is a heavy reformate feedstock comprising xylenes and C9 aromatics, said catalyst comprises at least one member of the MCM-22 family of molecular sieves, and the process further comprises a step of recycling at least a portion of said olefin-free product to contact said catalyst; and/or wherein the process includes a step, subsequent to said cycle time, of operating with (substantially) 100% recycled product as feedstream, without the addition of fresh feedstock, for a period of time sufficient to rejuvenate said catalyst, whereby said catalyst is then capable of removing said contaminants at a rate of at least 1000 kg of olefins per kg of catalyst under said conditions to produce a substantially olefin-free aromatics stream; and/or wherein said feedstock comprises a C8+ heavy reformate having a BI ranging from 750 to 1500, said feedstock further comprising <10 ppm benzene, <5000 pm toluene, and >50 wt % C8 aromatics, and wherein said substantially olefin-free aromatics stream has a BI of no more than 50. Still additional more preferred embodiments include: (a) a method for removing bromine-reactive contaminants from an aromatic hydrocarbon feedstream comprising: (a) providing an aromatic hydrocarbon feedstream having a diene level of less than 1000 ppm and a BI from about 100 to about 3000; and (b) contacting said aromatic feedstream with an acid active catalyst composition under conditions sufficient to at least partially remove bromine-reactive contaminants to provide both a treated aromatic hydrocarbon feedstream having a BI of no more than 50 ppm, and a used acid active catalyst composition having carbon deposits thereon, wherein said contacting includes conditions comprising a feedstream temperature of at least 210° C. at the start of the cycle to between about 250 and 300° C. at the end of the cycle, and at a WHSV of between 5 and 30, preferably between 10 and 20, from the start to the end of the cycle, which may include a yet still more preferred embodiment of a step, after said end of said cycle, wherein said acid active catalyst is regenerated (or rejuvenated—the terms are used synonymously herein) by contact with a feedstream of 100% (or substantially thereabout—at least an amount sufficient to rejuvenate within a reasonable time period) recycled product for a period sufficient to rejuvenate the catalyst, whereby said catalyst is capable of removing said contaminants at a rate of at least 1000 kg of olefins per kg of catalyst under said contacting conditions; (b) and also in a method for removing bromine-reactive contaminants from an aromatic hydrocarbon feedstream having less than 1000 ppm dienes and less than 10,000 ppm total olefins, comprising contacting a catalyst selected from the MCM-22 family of molecular sieves with said feedstream for a period of time defined as a contact cycle time, the improvement comprising operating said method under conditions sufficient for said catalyst to remove said contaminants from said feedstream at a rate of at least 1000 kg of olefins per kg of catalyst to produce a product comprising a substantially olefin-free aromatics stream during said cycle time and also to produce at least a portion of said spent catalyst not capable of removing said contaminants at said rate, and then contacting said spent catalyst with product and substantially without said feedstream for a time and under conditions sufficient to rejuvenate said spent catalyst to a condition capable of removing said contaminants at said rate under said conditions, which may yet still further be specified by the embodiment wherein said conditions include a feedstream temperature in the range of at least 210° C., preferably at least 215° C., or at least 220° C., or at least 225° C., at the start of the contact cycle time to a temperature in the range of about 240 to about 300° C., preferably between about 250° C. to about 300° C., or about 260° C. to about 300° C., or about 270° C. to about 300° C., or about 280° C. to about 300° C. at the end of said contact cycle time, and a WHSV of greater than 5 and less than 30, preferably between about 10 and 20; and/or wherein said substantially olefin-free product has a BI of about 50 or less.

What is claimed is:

1. In a method for removing bromine-reactive contaminants from an aromatic hydrocarbon feedstream having less than 1000 ppm dienes and less than 10,000 ppm total olefins, comprising contacting a catalyst selected from the MCM-22 family of molecular sieves with said feedstream for a period of time defined as a contact cycle time, wherein the improvement comprises conditions including heating said feedstream to a temperature in the range of at least 210° C. at the start of the contact cycle time to a temperature in the range of about 240 to about 300° C. at the end of said contact cycle time, and a WHSV of greater than 5 and less than 30, whereby said contaminants are removed at a rate of at least 1000 kg of olefins per kg of catalyst to produce a substantially olefin-free aromatics stream during said cycle time.

2. The method of claim 1, wherein said feed is a heavy reformate feedstock comprising xylenes and C9 aromatics, and the process further comprises a step of recycling at least a portion of said olefin-free product to contact said catalyst.

3. The method of claim 1 including a step, subsequent to said cycle time, of operating with 100% recycled product as feedstream, without the addition of fresh feedstock, for a period of time sufficient to rejuvenate said catalyst, whereby said catalyst is capable of removing said contaminants at a rate of at least 1000 kg of olefins per kg of catalyst under said conditions to produce a substantially olefin-free aromatics stream.

4. The method of claim 1, wherein said feedstock comprises a C8+ heavy reformate having a BI ranging from 750 to 1500, said feedstock further comprising <10 ppm benzene, <5000 pm toluene, and >50 wt % C8 aromatics, and wherein said substantially olefin-free aromatics stream has a BI of no more than 50.

5. A method for removing bromine-reactive contaminants from an aromatic hydrocarbon feedstream comprising:
(a) providing an aromatic hydrocarbon feedstream having a diene level of less than 1000 ppm and a BI from about 100 to about 3000; and
(b) contacting said aromatic feedstream with a catalyst selected from the MCM-22 family of molecular sieves under conditions sufficient to at least partially remove bromine-reactive contaminants to provide both a treated aromatic hydrocarbon feedstream having a BI of no more than 50 ppm, and a used acid active catalyst composition having carbon deposits thereon, wherein said contacting includes conditions comprising a feedstream temperature of at least 210° C. at the start of the cycle to between about 250° C. and 300° C. at the end of the cycle, and at a WHSV of between 5 and 30.

6. The method of claim 5, wherein after said end of the cycle, said acid active catalyst is regenerated by contact with a feedstream of 100% recycled product for a period sufficient period to rejuvenate the catalyst, whereby said catalyst is capable of removing said contaminants at a rate of at least 1000 kg of olefins per kg of catalyst under said contacting conditions.

7. In a method for removing bromine-reactive contaminants from an aromatic hydrocarbon feedstream having less than 1000 ppm dienes and less than 10,000 ppm total olefins, comprising contacting a catalyst selected from the MCM-22 family of molecular sieves with said feedstream for a period of time defined as a contact cycle time, the improvement comprising operating said method under conditions sufficient for said catalyst to remove said contaminants from said feedstream at a rate of at least 1000 kg of olefins per kg of catalyst to produce a product comprising a substantially olefin-free aromatics stream during said cycle time and also to produce at least a portion of said spent catalyst not capable of removing said contaminants at said rate, and then contacting said spent catalyst with said product and substantially without said feedstream for a time and under conditions sufficient to rejuvenate said spent catalyst to a condition capable of removing said contaminants at said rate under said conditions.

8. The process of claim 7, wherein said conditions include a feedstream temperature in the range of at least 210° C., at the start of the contact cycle time to a temperature in the range of about 240 to about 300° C., at the end of said contact cycle time, and a WHSV of greater than 5 and less than 30.

9. The process of claim 7, wherein said substantially olefin-free product has a BI of about 50 or less.

* * * * *